United States Patent
Lu

(10) Patent No.: US 9,833,219 B2
(45) Date of Patent: Dec. 5, 2017

(54) ANGLE ORIENTED ARRAY FOR MEDICAL ULTRASOUND

(71) Applicant: Siemens Medical Solutions USA, Inc., Malvern, PA (US)

(72) Inventor: Xuan-Ming Lu, Issaquah, WA (US)

(73) Assignee: Siemens Medical Solutions USA, Inc., Malvern, PA (US)

(*) Notice: Subject to any disclaimer, the term of this patent is extended or adjusted under 35 U.S.C. 154(b) by 638 days.

(21) Appl. No.: 14/226,729

(22) Filed: Mar. 26, 2014

(65) Prior Publication Data

US 2015/0272548 A1    Oct. 1, 2015

(51) Int. Cl.
| | |
|---|---|
| *A61B 8/08* | (2006.01) |
| *A61B 8/00* | (2006.01) |
| *G01S 15/89* | (2006.01) |
| *G01S 7/52* | (2006.01) |
| *B06B 1/06* | (2006.01) |

(52) U.S. Cl.
CPC ............ *A61B 8/5207* (2013.01); *A61B 8/445* (2013.01); *A61B 8/4483* (2013.01); *A61B 8/4488* (2013.01); *A61B 8/4494* (2013.01); *A61B 8/5215* (2013.01); *B06B 1/0607* (2013.01); *G01S 7/52079* (2013.01); *G01S 15/8915* (2013.01)

(58) Field of Classification Search
None
See application file for complete search history.

(56) References Cited

U.S. PATENT DOCUMENTS

| | | | | |
|---|---|---|---|---|
| 6,104,126 | A * | 8/2000 | Gilmore | B06B 1/0607 310/334 |
| 7,500,954 | B2 | 3/2009 | Wilser et al. | |
| 7,666,143 | B2 | 2/2010 | Wilser et al. | |
| 8,206,305 | B2 | 6/2012 | Garbini et al. | |
| 2003/0055308 | A1* | 3/2003 | Friemel | A61B 8/14 600/15 |
| 2006/0241468 | A1* | 10/2006 | Lu | B06B 1/0622 600/459 |

FOREIGN PATENT DOCUMENTS

WO    WO 2008066598 B1    8/2008

* cited by examiner

*Primary Examiner* — Katherine Fernandez
*Assistant Examiner* — Bradley Impink

(57) ABSTRACT

Volume scanning along different planes is provided using angling of the elements. Rather than orthogonal dicing of the slab, kerfs are formed at non-parallel and non-perpendicular angles to the azimuth axis of the array or longitudinal axis of the slab. Apertures formed from selected groups of the angled elements and/or parts of angled elements may be used to steer along planes that extend at an angle of 5 degrees or more away from the azimuth or longitudinal axis. By walking the aperture, different parallel planes are scanned with a one-dimensional array of elements.

11 Claims, 2 Drawing Sheets

ANGLE ORIENTED ARRAY FOR MEDICAL ULTRASOUND

BACKGROUND

The present embodiments relate to acoustic arrays for medical ultrasound. Acoustic arrays are formed from semiconductor or piezoelectric material. Piezoelectric materials include solid piezoelectric or composites. The materials transduce between acoustic and electrical energies.

The material is divided into elements, such as dicing a slab of piezoelectric material into a linear array of elements as shown in FIG. 2. By mounting on a rigid or semi-rigid backing, the array of elements maintains a desired planar emitting face. The arrangement of elements may be curved for a curved linear array. For example, an array formed from piezoelectric composite material is warped. The elements on the end are positioned away from an azimuth axis. The emitting face of the array is flat in elevation but curved along azimuth.

Two-dimensional arrays are used for three-dimensional imaging. Transducer material is divided into elements along two-dimensions. However, the number of elements becomes large. An alternative is to steer mechanically in one dimension, such as a one-dimensional array in a wobbler transducer. However, the mechanical steering requires space and adds complexity.

Acoustic arrays may be positioned in a catheter, endocavity probe, or other device for insertion into a patient. Due to the size of the catheter or probe, there may be limited space for conductors or mechanical structures. However, the ability to scan in three-dimensions from a catheter is desired, such as for ablation procedures. For example, U.S. Pat. No. 7,666,143 shows twisting a one-dimensional array in a catheter for volume imaging. As another example, U.S. Pat. No. 7,500,954 shows a multidimensional array that is hinged to expand for volume imaging. The hinge may use a memory metal for operation.

Other complex array geometries may be used. However, such arrays may require complex and expensive manufacturing techniques. Fixturing and components with machined parts that match the desired curvature may lead to high cost in materials, tooling, and labor. Twisting may place extra stress on the array, resulting in a greater failure rate in manufacturing and/or during use.

BRIEF SUMMARY

By way of introduction, the preferred embodiments described below include methods, systems, improvements, and transducers. Volume scanning along different planes is provided using angling of the elements. Rather than orthogonal dicing or forming of the slab, kerfs or elements separations are formed at non-parallel and non-perpendicular angles to the azimuth axis of the array or longitudinal axis of the slab. Apertures formed from selected groups of the angled elements and/or parts of angled elements may be used to steer along planes that extend at an angle of 5 degrees or more away from the azimuth or longitudinal axis. By walking the aperture, different parallel planes are scanned with a one-dimensional array of elements.

In a first aspect, an ultrasound transducer includes a slab of transducer material having a length greater than a width. A plurality of elements is formed from the transducer material of the slab. First kerfs separate the elements. The first kerfs extend across the width of the slab at a first non-normal angle by at least 10 degrees to an axis along the length.

In a second aspect, a system is provided for an acoustic transducer. A plurality of elements is in a one-dimensional array extending along an axis. The centers of the elements are along the axis, and the elements are angled by more than 10 degrees from the axis. A beamformer has channels connected with the elements. The beamformer is configured to scan from the elements along scan planes angled by more than 10 degrees from the axis due to the elements being angled by more than 10 degrees from the axis.

In a third aspect, a method is provided for scanning with an acoustic transducer. A first aperture is formed on an array of elements. The array of elements is formed such that the elements extending along an azimuth direction are angled away from the azimuth direction. A first plane is scanned with the first aperture. The first plane is not parallel to the azimuth direction. A second, different aperture is formed on the array of elements. The second aperture corresponds to walking the first aperture in the azimuth direction along the array of elements. A second, different plane is scanned with the second aperture. The second plane is not parallel to the azimuth direction and is parallel with the first plane. The second plane is spaced from the first plane by an amount of shift of the first aperture relative to the second aperture along the azimuth direction. A three-dimensional representation is generated as a function of data from the scanning and the relative positions of the first and second planes.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

Volume scanning with ultrasound typically uses a wobbler array or a multi-dimensional array. For locations with limited space, wobbler or multi-dimensional arrays may not be an option. One solution is a helically twisted array. Using a helical array twisted along an azimuth axis, different scan planes may be scanned. By walking an aperture along the azimuth axis, the angles of the acoustic planes vary. A volume may be sampled. The helical geometry and use of such an array are disclosed in WO 2008066598 and U.S. Pat. No. 8,206,305, the disclosures of which are incorporated herein by reference. The twisted array may be used in ultrasound cardiac catheters, transesophageal (TEE) probes, endocavity probes, or other transducer for insertion into a patient where limited space is provided. However, the apertures on a helical array are limited for two dimensional scanning.

Figure 2:
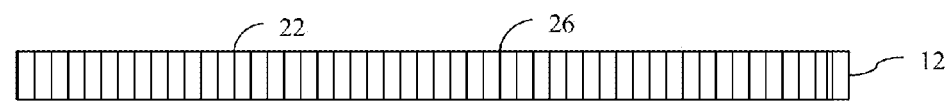
FIG. 2 illustrates a top view one-dimensional transducer array of the prior art.

The two-dimensional scanning, traditional one-dimensional arrays are diced perpendicular (elevation) to long axis (azimuth) (see FIG. 2). To provide for both two and three-dimensional scanning with a one dimensional array, the array is diced or elements formed at an angle (see FIG. 3). For elevation or space limited transducers (e.g., cardiac catheter), the elements formed by the angled dicing or separation allow off-axis steering. The same one-dimensional array may be used for scanning different planes in a volume and also used for two-dimensional scanning with a large or full aperture.

Figure 1:
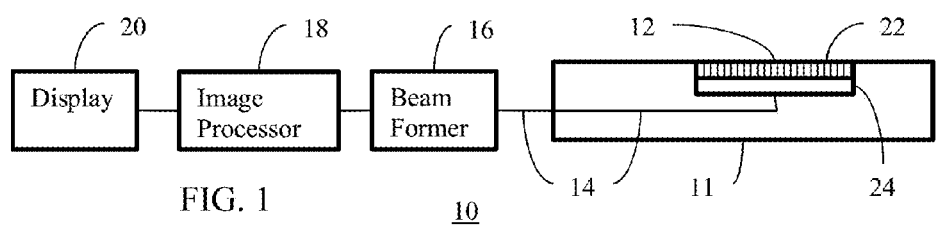
FIG. 1 is a graphical representation of an example transducer system used in a catheter or other probe.

FIG. 1 shows a system 10 for an acoustic transducer 11. In the example of FIG. 1, the acoustic transducer 11 is a cardiac catheter, intra-operative, endocavity, endovaginal, transesphogeal, or other ultrasound probe for insertion within a patient. In an alternative embodiment, the acoustic transducer 11 is a handheld probe for use external to the patient. For example, the acoustic transducer 11 is intended for imaging through a limited acoustic window, such as between the ribs. Due to the limited size of the probe and/or acoustic window, a two-dimensional probe for volume imaging may not be provided. Instead, the array 12 of elements 22 is a one-dimensional array and/or has a limited elevation width. In other embodiments, the acoustic transducer 11 has sufficient space for a multi-dimensional array.

The system 10 includes the array 12 of elements 22, conductors 14, a beamformer 16, an image processor 18, a display 20, and a switch network 24. Additional, different, or fewer components may be provided. For example, the system 10 includes the array 12 and conductors 14 without the beamformer 16, image processor 18, and/or display 20. These imaging electronics may be in a separate ultrasound imaging system. The transducer releasably connects with the imaging system. As another example, the switch network 24 is provided as part of the beamformer 16 outside of the acoustic transducer 11.

The array 12 and conductors 14 are connected with or positioned in the transducer probe. A window or lens is over the array 12 for acoustic scanning from an emitting face of the array from within the probe. The array 12 is shown in FIG. 1 as a side view.

The array 12 has a plurality of elements 22, backing material, electrodes 21, and matching layers. Each element 22 is sandwiched between electrodes 21. One of the electrodes 21 of each element 22 is electrically isolated from other elements for separate connection to beamformer channels. Additional, different, or fewer components may be provided. For example, two or more matching layers are used. As another example, a chamber is provided instead of backing material. The backing material absorbs acoustic energy to limit or prevent reflections received from a back of the array 12. The matching layers provide a more gradual transition between acoustic impedance, minimizing reflection from the boundary between the transducer and the patient. The electrodes 21 interact with the elements 22 to transduce between acoustic and electrical energy. The variation of potential or distance between electrodes across an element causes electrical signal generation or acoustic energy, respectively.

The elements 22 contain piezoelectric material. Solid or composite piezoelectric materials may be used. Each element is a solid, cubic, or six sided, but other shapes or surfaces may be provided. For example, the emitting face of one or more elements 22 is concave or convex for elevation focusing or frequency based directivity. Alternatively, a microelectromechanical or capacitive device, such as a flexible membrane, is used. Any now known or later developed ultrasound transducer may be used. Longer elements in elevation as compared to wavelength may provide increased elevation directivity.

Any number of elements 22 may be provided, such as 64 elements, 128 elements or other number of elements 22 to allow for more or larger apertures. The elements 22 are adjacent each other, such as having substantially wavelength or less spacing between the centers of adjacent elements 22. For example, the elements 22 have half wavelength spacing with kerfs 26 acoustically separating each element 22. Other methods of element separation may be used. The wavelength spacing is based on a center, average, imaging or other frequency of operation of the array 12. Sparse arrays 12 with greater spacing between elements 22 may be used.

The elements 22 are positioned along an azimuth axis 25 (see FIG. 3) of the array 12. For a one-dimensional array 12, the elements 22 are in a single row along the azimuth axis 25. Thirty-two, fifty or more, sixty-four, one hundred and twenty eight or other numbers of elements 22 may be used. The array 12 may be linear or curved linear. A curved linear array 12 has ends or a middle that extend towards or away from the azimuth axis 25, but the elements 22 are still positioned along the azimuth dimension. Due to the curve, some elements 22 of the array 12 are at different depths or ranges (e.g., into or out of the page of FIG. 3).

The side (top) of the elements 22 covered by the matching layer, closer to the region to be scanned, and/or opposite the backing material is the emitting face. Acoustic energy is transmitted from and received at the emitting face of the array 12. The angle of acoustic energy relative to the emitting face affects the sensitivity of the elements 22 to the energy. The elements 22 are more sensitive to the energy at normal incidence to the elements 22.

The elements 22 of the array 12 are formed from a slab 23 of material. For example, a slab 23 of piezoelectric or piezoelectric composite material is provided. For capacitive microelectromechanical transducer material, the slab 23 is a slab 23 of semiconductor material (e.g., silicon). The slab 23 has any dimensions, such as being 1-5 cm long, 0.5-2 cm wide, and 0.1-1 cm high. The length is greater than the width. A rectangular or cuboid slab 23 is provided. The slab 23 is flat or without curve, but may be curved in other embodiments. The opposite sides of the slab 23 are parallel to each other and straight. Each corner is formed from edges intersecting orthogonally, perpendicularly, and/or at 90 degrees plus or minus 2 degrees. Alternatively, other shapes are provided.

In an alternative embodiment, the slab 23 is twisted into a helical pattern. After or before formation of the elements 22 in the slab 23, the slab 23 is twisted about the longitudinal axis 25. Memory metal, application of mechanical stress, or mounting to a fixture may be used to twist the slab 23. The elements 22 are twisted in a helical pattern about the azimuth axis 25. The amount of twist may be increased and/or the stress from the twisting on the array 12 reduced due to the angle used for the elements 22.

To form the elements 22, kerfs 26 are cut into the slab 23. The kerfs 26 are channels between elements 22. The kerfs 26 extend completely through the slab 23 of transducer material, but may extend over half way but less than all of the way through the slab 23. The kerfs 26 are formed by a dicing saw, laser, or other dicing operation. The kerfs 26 are thin relative to the elements 22, such as having a width less than ½, less than ¼, or less than ⅛ of the elements 22.

In an alternative embodiments, such as for a CMUT, the elements 22 are formed with electrical isolations or other separation between elements 22. Instead of a kerf, the elements 22 are formed by deposition, etching, or other process as acoustically and/or electrically separate components at the angled orientation.

A plurality of parallel kerfs 26 are formed in the slab 23. The kerfs 26 extend from edge to edge across the width of the slab 23. The kerfs 26 are straight, such as associated with a cut using a saw. In alternative embodiments, the kerfs 26 may deviate from straight.

Figure 3:
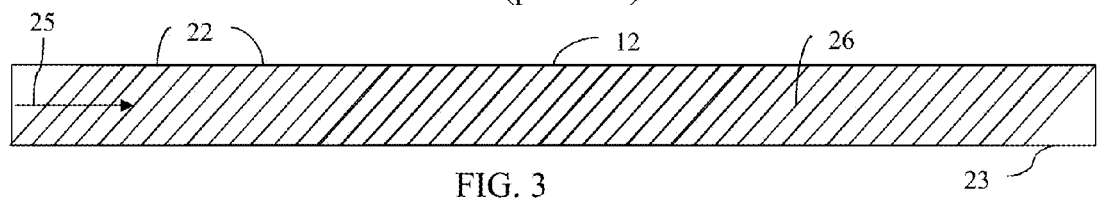
FIG. 3 illustrates one embodiment of a top view of a transducer array with angled elements.

FIG. 2 shows a top view (view looking down at the emitting face) of the kerfs 26 at right angles to the longitudinal axis 25 of the array 12. Rather than using this perpendicular arrangement, the kerfs 26 are formed across the width at a non-normal angle to the azimuth axis of the array 12. Any angle may be used. FIG. 3 shows a top view of an angle of about 45 degrees (about being for +/−2 degrees). The angle may be 30 degrees. Other angles from 10-80 degrees, 5-85 degrees, 20-70 degrees, 30-60 degrees, or 40-50 degrees may be used. In one embodiment, the angle is about 5-30 degrees from perpendicular to the azimuth axis 25 or otherwise matches a twist rate of a helical or twisted array. The elements 22 are rotated about the range axis of the array 12 (i.e., rotated in the elevation-azimuth plane). The array 12 is not rotated about the range axis, but may be.

The kerfs 26 for elevation extending elements 22 have an elevation length greater than the width of the slab 23. The centers of the elements 22 are along the azimuth or longitudinal axis 25.

For selecting apertures of the elements that scan in a plane other than along the azimuth axis 25, cross kerfs 28 are formed in the slab 23. The cross kerfs 28 are a same or different depth as the kerfs 26. The cross kerfs 28 are a same length or different length as the kerfs 26. The cross kerfs 28 extend from one edge to another edge across the width of the slab 23. The kerfs 26 and/or cross kerfs 28 at the ends of the slab 23 may extend only part way across the width due to the angle.

The cross kerfs 28 are also at a non-normal angle to the azimuth axis 25 of the array 12. Any of the angles (e.g., 10 or more (30-60) degrees to the elevation and/or azimuth axis 25) mentioned above for the kerfs 26 may be used for the cross kerfs 28. In alternative embodiments, the cross kerfs 28 are normal or perpendicular to the azimuth axis 25.

The cross kerfs 28 are at a different angle than the kerfs 26 relative to the azimuth axis 25. For example, the cross kerfs 28 are at an angle 10 degrees rotated from the kerfs 26. The cross kerfs 28 are rotated to be at an angle on an opposite side of the elevation axis of the array 12 than the kerfs 26, such as the cross kerfs 28 being 90 degrees from the kerfs 26. Greater or lesser rotation (e.g., 60-120 degrees) may separate the kerfs 26 from the cross kerfs 28.

The cross kerfs 28 form segments 30. Any number of segments 30 are created along the array 12, such as ten or more (e.g., 32). The segments 30 are wider than the elements 22, such as being more than three elements 22 wide. The segments 30 are an integer number of elements 22 wide, but may have fractional width relative to the elements 22. Each segment 30 has a same or different length as the elements 22.

The cross kerfs 28 to form the segments 30 separate one or more elements 22. The elevation extent of the elements 22 is separated into sub-elements 32 by the cross kerfs 28. A given element 22 may be separated into two or more sub-elements 32. Different elements 22 may have the same or different numbers of sub-elements 32. Using switching, the sub-elements 32 of each element 22 are electrically connectable with each other. The sub-elements 32 of a given element 22 are not electrically connectable with other elements 22, but may be in other embodiments. Despite the separation into sub-elements 32, the sub-elements 32 of a given element 22 within a scanning aperture connect to a same beamformer channel so share a signal to operate as the element 22.

Figure 4:
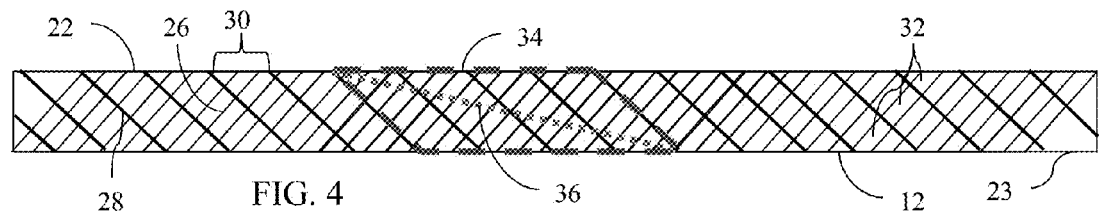
FIG. 4 illustrates another embodiment of a top view of a transducer array with angled elements and a selected aperture for scanning an angled scan plane.

Due to the kerfs 26, the elements 22 are angled by more than 5 or 10 degrees from the longitudinal and/or azimuth axis. For example, the elements 22 are angled by 30-60 degrees from the azimuth axis 25. Given the element 22 position of the centers along the azimuth axis 25, off-axis steering may not be provided. Due to the cross kerfs 28, apertures of the elements 22 may be defined that allow for off-axis steering. The cross kerfs 28 are at a different angle than the kerfs 26 for defining off-axis steerable apertures on the array 12. FIG. 4 shows an example scan aperture 34 for off-axis steering. The scan aperture 34 may be selected based on segments 30 to provide for an aperture 34 that steers at angles other than in a plane parallel or along the azimuth axis 25, even for the one-dimensional array of elements 22.

Referring again to FIG. 1, the switches 24 electrically connect the sub-elements 32 of respective elements 22 together when in the selected aperture 34. The switches 24 allow common signals to be shared by the sub-elements 32 of each given element 22 in the aperture 34. A single beamformer channel connects with a given element 22 and not the other elements 22. For a symmetric delay pattern, a beamformer channel may connect with multiple elements 22. To provide the channel signals to multiple sub-elements 32 of an element 22, the switch 24 between sub-elements 32 or connecting sub-elements to the beamformer channel is closed. If the sub-element 32 is not part of the segment 30 included in the aperture 34, the switch 24 for that sub-element 32 is opened.

In one embodiment, the switches 24 are part of a multiplexer or other network of controllable switches. The multiplexer is configured by control signals to select segments 30 and the aperture 34 for volumetric imaging. To scan a volume, the switches 24 operate to select different segments 30 and apertures 34 at different times or for scanning different planes in a walking or shifted aperture 34.

The switches 24 are in a chip, such as an application specific integrated circuit or a multiplexer chip. In one embodiment, pre-amplifiers and/or a partial beamformer are included in the chip with the switches 24. As a chip, the switches 24 may be bump soldered adjacent to the array 12. The chip itself may provide a hard acoustic backing structure, allowing for direct bump soldering to electrodes of the elements 22. Soft backing may be positioned against the chip, sandwiching the chip with the array 12. In other embodiments, z-axis wire bonds or other conductors extend the electrodes from the elements 22 through backing material for connection (e.g., bump soldering, wire bonding, and/or connection through traces on flexible circuit material) with the chip. The chip is adjacent to the array 22, but separated by the backing from the array 12.

Referring to FIG. 1, the electrical conductors 14 are cables, coaxial cables, traces, wires, flex circuits, wire jumpers, combinations thereof, or other now known or later developed conductor. The conductors 14 electrically connect the electrodes 21 of the array 12 with a connector of the transducer probe or the beamformer 16. One or more conductors 14 are provided for each element 22. Alternatively, fewer conductors 14 than elements 22 may be used, such as for switched apertures, partial beamforming, or multiplexing. The conductors 14 are separately addressable. Each element 22 may be selectively used for a given aperture and associated electronic steering. Alternatively, some elements 22 are useable with only a subset of possible apertures.

In one embodiment, the array 12 is positioned within a catheter. The array 12 may fit within a 10-15 French, 3.33 mm, or other diameter catheter. The conductors 14 are routed through the catheter to the beamformer 16. The catheter transducer is used for imaging. The images assist in diagnosis, catheter or tool guidance, and/or therapy placement. The geometry may assist in imaging. For example, maintenance of the array 12 as flat or curved with the catheter may reduce imaging artifacts and/or allow sector scanning. By including the angle element array 12 within the catheter, three-dimensional scanning and image representations may be used. Alternatively, the angled elements 22 of the array 12 are used in other transducers.

The beamformer 16 includes a plurality of channels for generating transmit waveforms and/or receiving signals. Relative delays and/or apodization focus the transmit waveforms or received signals for forming beams. The beamformer 16 connects with the conductors 14. The beamformer 16 selects an aperture including one, some, or all of the elements 22 of the array 12. Different apertures may be used at different times. The aperture is formed by using the elements 22 for transmit and/or receive operations while not using other elements 22. The beamformer 16 is operable to scan from a plurality of apertures formed by adjacent groups of the elements 22. The apertures may walk through regular increments or skip to different portions of the array 12.

FIG. 4 shows a top view of one example aperture 34. Any number of segments 30 is selected, resulting in selection of corresponding elements 22. The number of segments 30 used determines the angle of the scan plane 36. FIG. 4 shows four segments 30, but greater or lesser numbers may be used. There are more elements 22 than segments 30 for the aperture 34.

For the selected aperture 34, all of some elements 22 are included. Other elements 22 only have less than all of the sub-elements 22 within the aperture 34. The switches 24 are controlled to connect or disconnect sub-elements 32 with each other and the respective beamformer channels. In the example of FIG. 4, four elements 22 include the entire elevation extent or across width extent, while thirteen elements 22 include only parts of the elements 22. Other ratios may be provided. By not including parts of some elements 22 in the aperture 34, the angle of the elements 22 may be used, in part, to shift the centers of the effective elements of the aperture to a line 36 different from the longitudinal axis of the array 12. The azimuth axis of the aperture 34 is different from the azimuth axis 25 of the array.

For scanning, the beamformer 16 electronically focuses along a direction dictated by the effective centers of the elements 22. Since some of the elements 22 are partial, and angled and the aperture 34 and corresponding segments 30 are also angled, and the center of the aperture 34 extends at an angle rotated in the azimuth-elevation plane away from the azimuth axis 25 of the array 12. The intersection of the scan plane 40 (see FIG. 5) with the array 12 is represented by the line 36. This line or axis along which steering for the scan plane 40 occurs is rotated by 5 or more degrees from the azimuth axis 25. The angle diced array 12 makes it possible to steer ultrasound beams off axis of the array 12, since the element maximum directivity is off the long axis (azimuthal axis 25).

A plurality of scan lines using an aperture 34 is scanned. The scan lines are in the scan plane 40. During receive operations, the focus may vary as a function of depth. An array or aperture elevation focus is provided by a lens and/or element sensitivity, or the array 12 or aperture is not focused in elevation. In alternative embodiments, the beamformer 16 connects with elevation spaced elements or sub-elements for at least partial electric focusing and/or steering in the elevation dimension.

In the angled array geometry, different planes 40 are scanned by scanning from different apertures 34 of the array 12. For example, the aperture 34 shifts along the azimuth direction by one or more segments 30. The size of the aperture 34 (e.g., number of segments 30) is the same, but may vary by aperture 34. Different elements 22 form the different apertures 34. A given element 22 may be used in only one aperture 34 or may be used in multiple different apertures 34, depending on the step size of the shift in the aperture 34. Similarly, the same or different sub-elements 32 of a given element 22 may be used for different apertures 34.

With each shift in the aperture 34, the line 36 also shifts along azimuth of the array 12. The line 36 of each aperture 34 has a same angle but different azimuth position, resulting in parallel scan planes 40 along the array 12. The parallel scan planes 40 are all at the same angle away from the azimuth axis. Using different apertures with some or all elements 22 not in common allows for scanning different planes or regions.

In alternative embodiments, the number of segments 30 changes for different apertures 34, so the angle of the scan plane 40 and corresponding line 36 varies. The scan planes 40 are not parallel, but at least some lines 36 are rotated from the azimuth axis 25.

The size of each aperture 34 may be limited by the desired angle of the line 36 and scan plane 40. Longer apertures 34 shift the line 36 closer to (smaller angle from) the azimuth axis 25 of the array 12. Shorter apertures 34 (i.e., fewer segments 30) provide a greater rotation of the line 36, but may have less desirable scan qualities. The total number of independent beams that can be formed by an array is on the order of the number of elements 22 of an aperture 34. By varying the number of segments 30 in the different apertures 34, there is a tradeoff between (a) resolution and signal-to-noise and (b) the angle of the line 36.

The aperture may be formed for a scan plane that intersects the array 12 along the azimuth axis 25. For example, the aperture is formed from all of the elements 22 and corresponding segments 30 or at least from a greater number than for the walking apertures in volume scanning. By using the large number of segments 30 and corresponding elements 22 and/or using all of the sub-elements 32 of each element 22, the line 36 is along or less than 5 degrees from the azimuth axis 25. This allows for two-dimensional scanning as if the array 12 of FIG. 2 were used. For example, the full azimuth extent of elements 22 on a planar or curved array 12 are used for conventional 2D imaging, which may not be possible with a helically twisted array. Alternatively, two-dimensional imaging is provided using one of the apertures 34 used for volume scanning.

The image processor 18 is a detector, filter, processor, application specific integrated circuit, field programmable gate array, digital signal processor, control processor, scan converter, three-dimensional image processor, graphics processing unit, analog circuit, digital circuit, or combinations thereof. The image processor 18 receives beamformed data and generates images on the display 20. The images are associated with a two-dimensional scan.

Alternatively or additionally, the images are three-dimensional representations. Data representing a volume is acquired by scanning along different planes using the walking or different apertures 34. The processor 18 generates a three-dimensional data set as a function of the scanning by the beamformer. The data of the three-dimensional data set may be interpolated to a Cartesian grid or maintained in a scan format. The relative position of the planes used for scanning may be known or assumed based on the aperture position, angle of the elements 22 and angle of the segments 30. Any rendering may be used, such as projection, volume, and/or surface rendering. The processor 18 generates the three-dimensional representation from the data representing the volume.

Figure 5:
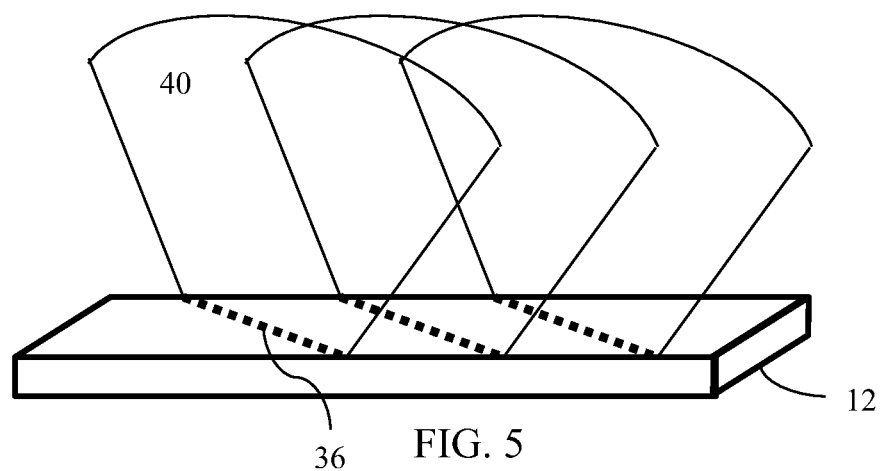
FIG. 5 illustrates a position of a scan plane relative to an array according to one embodiment.

A volume scan may be obtained with the array 12 having angled elements 22. By using the angles of the elements 22 and segments 30, different scan planes 40 within a volume may be scanned. FIG. 5 shows three parallel scan planes 40, but more or fewer may be provided. The scan planes 40 are spaced apart in the azimuth and elevation dimensions of the array 12, such as extending at the angle of the line 36 but from different positions along the array 12. Three-dimensional volume imaging may be achieved by walking the aperture 34 along azimuth (long axis) of the array 12 and stacking images which represent regions at a non-normal angle to elevation dimension (short axis) of the array 12 without twisting array. By electric steering along the line 36 for each line 36 and corresponding scan plane 40, the scans are of the volume.

Alternatively, the array 12 includes twist. The twist results in the scan planes 40 of the different apertures 34 having greater offset from each other in the elevation dimension relative to the array 12. Other volume scanning techniques may supplement the angled elements 22. A volume may be scanned by movement of the array 12 and/or the probe. In other embodiments, a multidimensional array 12 or an array with concave or convex elements 22 allows electronic or frequency steering, respectively, to scan a volume.

The display 20 is a monitor, CRT, LCD, or other display. One or more images are provided on the display. Two-dimensional or three-dimensional imaging is shown to the user.

Figure 6:
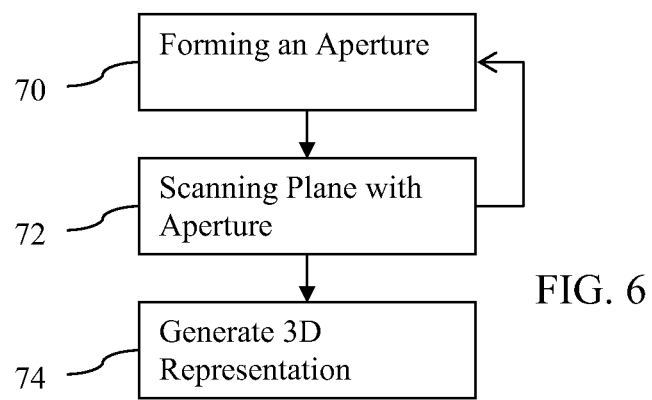
FIG. 6 is a flow chart diagram of one embodiment of a method for using an acoustic array with angled elements.

FIG. 6 shows a method for scanning with an acoustic transducer. The method uses the system 10 and/or array 12 of FIGS. 1, 3, and/or 4, or a different array and/or system. Additional, different, or fewer acts may be provided. For example, data representing a volume may be used without generating a three-dimensional representation in act 74. As another example, the repetition of acts 70 and 72 represented by the feedback arrow is not performed, such as where two-dimensional imaging using the angled elements is provided. The acts are performed in the order shown, but may be performed in other orders.

The method is performed with an array in a cardiac catheter or other space limited probe (e.g., endocavity or endovaginal probe) or probe for a space limited acoustic window (e.g., limited width for scanning between ribs). After positioning the probe within or against the patient, the array with angled elements is used to scan the patient for two and/or three-dimensional imaging.

In act 70, an aperture is formed on the array of elements. The aperture is all of the elements or a subset of the elements. Any size aperture may be used. The aperture includes contiguously adjacent elements or is sparse. The aperture is formed by connection of conductors and associated elements to the beamformer. Sub-elements for each element within the aperture are electrically connected together and/or with the same beamformer channel. Sub-elements not within the aperture are disconnected from the respective elements and beamformer channels. The elements, whether entire or partial, used for transmitting and/or receiving during a given transmit and receive event define the aperture. A different aperture may be used for transmit than for receive.

The aperture may be formed by switches as controlled by the beamformer or other controller. Contiguous or discontinuous segments are included in the aperture. By using angled elements and cross angled segments, the aperture defines the angle of the scan plane relative to the longitudinal dimension of the array. The angle is greater than 5 degrees (e.g., 10-45 degrees).

In act 72, a scan plane is scanned using the formed aperture. Using electronic focus or steering, transmit and receive beams are formed using the elements of the aperture. By changing the focus, a planar region may be scanned sequentially using the aperture. Single or multiple beams may be formed for transmit and/or receive operations for each event. Plane wave, diverging wavefront, or unfocused transmission may be used. Different apertures may be used for transmit and receive operations. In response to the transmission and reception with the aperture, data representing the scanned region (i.e., scan plane) is acquired.

The angle of the elements and the angle of the segments result in the acquired data representing the region at a particular rotation. The scan plane is not parallel to the azimuth direction of the array. Instead, the azimuth direction of the aperture is rotated from the azimuth direction of the array. As shown in FIG. 5, the scan plane 40 is at an angle to the longitudinal axis of the array 12. The line 36 is not parallel to the centers of the elements of the array. The electronic steering is in the scan plane 40 defined by the aperture, which shifts the angle of the plane relative to the array.

To scan a volume, acts 70 and 72 are repeated for different apertures and corresponding scan planes. Another aperture is formed and the associated region is scanned. By selecting a different aperture, a different plane is scanned. The position of the plane corresponds to shifting the angled scan plane along the longitudinal axis of the array. Other apertures are formed for scanning other regions or planes. The planes are parallel but spaced apart. The spacing corresponds to the amount of shift of the aperture along the array. The angle of the scan plane away from the azimuth direction of the array allows for scanning a volume (i.e., different planes) with different apertures.

In one embodiment, a walking aperture is used. The aperture shifts by one or more segments for each repetition. Data representing a number of different planes corresponding to the number of segments and/or number of segments divided by the shift size is acquired. The regions scanned are parallel, providing data for a volume rather than just one plane.

In act 74, a three-dimensional representation is generated. The data obtained from the scan is formatted for rendering. For example, the data is interpolated to a three-dimensional evenly spaced grid. As another example, the data for each plane or scan is scan converted into a two-dimensional data set. The two-dimensional data sets associated with each plane are provided for rendering. In another example, the data is maintained in an acquisition format, such as a polar coordinate format. The known plane positions, sample depth, and scan line position provide relative spatial positioning information for each datum.

The three-dimensional representation is rendered as a function of the data from the scanning. The relative positions of the scan planes are used to format the data and/or for rendering. Any now known or later developed rendering may be used. For example, using either view-based diverging lines or parallel lines along a viewing direction, projection rendering is provided. Minimum, maximum, first value over a threshold, average, alpha blending or other projection techniques may be used. Surface rendering may be used. Opacity, shading, or other rendering refinements may be applied.

The result of the rendering is a three-dimensional representation from a given viewing direction. The rendering may be performed from another viewing direction with a same set of data. For real-time imaging, the viewing direction may change for subsequently acquired data sets. Real-time three-dimensional imaging may be provided. The three-dimensional representation is an ultrasound image. The data is B-mode, intensity, Doppler mode, velocity, energy, harmonic mode, contrast agent, combinations thereof, or other types of ultrasound data.

Using the three-dimensional representation, tissue structure adjacent the array may be viewed. In the catheter or TEE embodiment, tissue structure of one heart chamber may be viewed from another heart chamber or the same heart chamber. Given the aperture spacing, the near views may provide less volume information for rendering. The array may be positioned a little away from the region to be scanned for higher resolution. The array may be rotated to further increase the volume field of view.

In addition or as an alternative to three-dimensional imaging, two-dimensional images are generated by scanning a single plane or region. Where the array continually twists, the aperture may be limited to scan a single plane. Where the array does not twist, the entire array may be used for two-dimensional imaging even though the array may also be used to scan a volume without mechanical motion of the array.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

I claim:

1. An ultrasound transducer system comprising:
   a slab of transducer material having a length greater than a width;
   a plurality of elements formed from the transducer material of the slab, the plurality of elements forming a one-dimensional array along the length and each element extending across the entire width of the slab; and
   first kerfs separating the plurality of elements, the first kerfs extending across the width of the slab at a first non-normal angle by at least 10 degrees to an axis along the length, wherein the plurality of elements are at the first non-normal angle.

2. The ultrasound transducer system of claim 1 wherein the transducer material comprises piezoelectric material.

3. The ultrasound transducer system of claim 1 wherein the slab comprises a rectangular block having first edges along the length, the first non-normal angle being between 30-60 degrees to the first edges.

4. The ultrasound transducer system of claim 1 wherein the first kerfs comprise a plurality of parallel, straight cuts at the first non-normal angle.

5. The ultrasound transducer system of claim 1 further comprising second kerfs at a second non-normal angle by at least 10 degrees to the axis along the length, the second non-normal angle being at least 10 degrees different than the first non-normal angle.

6. The ultrasound transducer system of claim 5 wherein the first non-normal angle is chosen such that it is 60-120 degrees different from the second non-normal angle when the second non-normal angle is between 30-60 degrees from the axis.

7. The ultrasound transducer system of claim 5 wherein the second kerfs separate the plurality of elements into sub-elements, the sub-elements connected with switches each configured to apply a common signal for a respective element.

8. The ultrasound transducer system of claim 7 wherein the switches are in a chip, the chip bump soldered adjacent to the slab.

9. The ultrasound transducer system of claim 1 wherein the slab is twisted in a helical pattern.

10. The ultrasound transducer system of claim 1 wherein the plurality of elements are in a catheter.

11. The ultrasound transducer system of claim 1 further comprising electrical connections to beamformer channels, the electrical connections and the plurality of elements arranged to scan from the plurality of elements along scan planes angled by more than 10 degrees from the axis due to the plurality of elements being angled by more than 10 degrees from the axis.

* * * * *